(12) United States Patent
Han et al.

(10) Patent No.: US 10,031,097 B1
(45) Date of Patent: Jul. 24, 2018

(54) ELECTRICAL RESPONSE USING NANOTUBES ON A FIBROUS SUBSTRATE

(71) Applicant: The United States of America, as Represented by the Administrator of the National Aeronautics & Space Administration (NASA), Washington, DC (US)

(72) Inventors: Jin-Woo Han, San Jose, CA (US); Meyya Meyyappan, San Jose, CA (US)

(73) Assignee: The United States of America as Represented by the Administrator of NASA, Washington, DC (US)

( * ) Notice: Subject to any disclaimer, the term of this patent is extended or adjusted under 35 U.S.C. 154(b) by 759 days.

(21) Appl. No.: 14/195,129

(22) Filed: Mar. 3, 2014

Related U.S. Application Data

(60) Provisional application No. 61/772,681, filed on Mar. 5, 2013.

(51) Int. Cl.
*G01N 27/48* (2006.01)
*G01N 27/22* (2006.01)
(Continued)

(52) U.S. Cl.
CPC ............ *G01N 27/048* (2013.01); *B82Y 15/00* (2013.01); *B82Y 30/00* (2013.01); *G01N 27/121* (2013.01);
(Continued)

(58) Field of Classification Search
CPC .. B82Y 30/00; B82Y 15/00; G01N 2291/014; G01N 2291/0255; G01N 2291/0256;
(Continued)

(56) References Cited

U.S. PATENT DOCUMENTS

| 7,013,700 B2* | 3/2006 | Rombach | G01N 25/56 73/1.06 |
| 7,276,266 B1* | 10/2007 | Khare | B82Y 30/00 427/294 |

(Continued)

OTHER PUBLICATIONS

Douglas R. et el., Carbon Nanaotube Gas and Vapor Sensors,2008, Wiley-VCH Verlag GmbH & Co. KGaA, Weinhem,ed. 2008, 47, 6550-6570.*

(Continued)

*Primary Examiner* — Randy Gibson
*Assistant Examiner* — Gedeon M Kidanu
(74) *Attorney, Agent, or Firm* — Christopher J. Menke; Robert M. Padilla; Mark P. Dvorscak

(57) ABSTRACT

A device produces an electrical signal in response to a stimulus. The device is formed of a flexible substrate including a layer of fibers, for example, paper, and a solution of dispersed carbon nanotubes coated onto and within the fibers, the solution evaporated to leave carbon nanotubes intertwined within the layer of fibers. The carbon nanotubes are functionalized to be optimized for producing an electrical signal for a particular stimulus, where the stimulus includes exposure of the device to a particular gas or vapor. A number of such devices, some or all of which can be different, are housed together, for producing a complex electronic signal, or for sensing any of a wide variety of stimulus.

20 Claims, 9 Drawing Sheets

(51) Int. Cl.
  *G01N 27/12* (2006.01)
  *B82Y 30/00* (2011.01)
  *B82Y 15/00* (2011.01)
  *G01N 27/04* (2006.01)

(52) U.S. Cl.
  CPC ......... G01N 27/223 (2013.01); *Y10S 977/953* (2013.01)

(58) Field of Classification Search
  CPC . G01N 2291/02845; G01N 2291/0426; G01N 29/022; G01N 27/223; G01N 27/121
  USPC ............................................. 73/24.04, 335.02
  See application file for complete search history.

(56) References Cited

U.S. PATENT DOCUMENTS

| | | | | |
|---|---|---|---|---|
| 7,767,270 | B1* | 8/2010 | Khare | B82Y 30/00 427/294 |
| 7,801,687 | B1* | 9/2010 | Li | G01N 27/127 422/83 |
| 7,939,734 | B1* | 5/2011 | Li | G01N 27/3277 204/400 |
| 7,968,054 | B1* | 6/2011 | Li | G01N 27/127 422/68.1 |
| 8,568,027 | B2* | 10/2013 | Ivanov | B82Y 30/00 374/143 |
| 2005/0081625 | A1* | 4/2005 | Chen | B82Y 30/00 73/335.02 |
| 2010/0089772 | A1* | 4/2010 | Deshusses | G01N 27/127 205/781 |
| 2010/0116666 | A1* | 5/2010 | Park | B82Y 30/00 204/571 |
| 2011/0167894 | A1* | 7/2011 | Samuilov | G01N 27/127 73/25.05 |
| 2012/0237680 | A1* | 9/2012 | Brahim | B82Y 30/00 427/249.1 |
| 2014/0151111 | A1* | 6/2014 | Shah | H05K 9/009 174/388 |

OTHER PUBLICATIONS

Schubert, et al., A Polymide-Based Capacitive Humidity Sensor, IEEE Trans, Electron Devices, Jul. 1985, 1220-1223, 32-7, IEEE.
Mitschke, Fiber-optic sensor for humidity, Opt. Lett., Sep. 1, 1989, 967-969, 14-17, Optical Society of America.
Collins, et al., Extreme Oxygen Sensitivity of Electronic Properties of Carbon Nanotubes, Science, Mar. 10, 2000, 1801-1804, 287, www.sciencemag.org.
Pascal-Delannoy, et al., Quartz Crystal Microbalance (QCM) used as humidity sensor, Sens. Actuators A, Sep. 1, 2000, 285-291, 84, Elsevier Science S.A.
Zahab, et al., Water-vapor effect on the electrical conductivity of a single-walled ca . . . , Phys. Rev. B 2000, Oct. 15, 2000, 10000-10003, 62-15, The American Physical Society.
Ho, et al., Chemiresistor-type NO gas sensor based on nickel phthalocyanine thin films, Sensors and Actuators B, Chemicalo, Jun. 15, 2001, 253-259, 77, Elsevier Science B.V.
Qiu, et al., A CMOS humidity sensor with on-chip calibration, Sens. Actuators A, Phys., Aug. 1, 2001, 80-87 92, Elsevier Science B.V.
Chopra, et al., Selective gas detection using a carbon nanotube sensor, Applied Physics Letters, Sep. 15, 2003, 2280-2282, 83-11, American Institute of Physics.
Li, Chemical Sensors, Chapter 9, Carbon Nanotube Applications: Chemical and Physical Sensors, 2004, CRC Press, Boca Raton, Florida.
Star, et al., Sensing with Nation Coated Carbon Nanotube Field-Effect Transisters, Electroanal., Jan. 26, 2004, 108-112, 16-1-2, Wiley-VCH Verlag GmbH & Co. KGaA, Weinheim.
Wan, et al., Positive temperature coefficient resistance and humidity sensing properties . . . , Appl. Phys. Lett, Apr. 19, 2004, 3085-3087, 84-16, American Institute of Physics.
Huang, et al., Carboxylation multi-walled carbon nanotubes modified with LiClO4 for water vapour detection, Nanotechnology, Jul. 23, 2004, 1284-1288, 15, IOP Publishing LTD, UK.
Kim, et al., Organic TFT Array on a Paper Substrate, IEEE Electron Device Lett., Oct. 2004, 702-704, 25-10, IEEE.
Fan, et al., ZnO nanowire field-effect transistor and oxygen sensing property, Applied Physics Letters, Dec. 13, 2004, 5923-5925, 85-24, American Institute of Physics.
Packirisamy, et al., A polyimide based resistive humidity sensor, Sensor Review, 2002, 271-276, 25-4, ProQuest.
Na, et al., Investigation of the humidity effect on the electrical properties of s . . . , Appl. Phys. Lett., Aug. 22, 2005, 093101-1-093101-3, 87 American Institute of Physics.
Su, et al., In situ synthesized composite thin films of MWCNTs/PMMA doped with KOH as a resistive humidity sensor, Sens. Actuators B, Dec. 28, 2006, 303-308, 124, Elsevier B.V.
Kuang, et al., High-Sensitivity Humidity Sensor Based on a Single SnO2 Nanowire, J. Am. Chem. Soc, Apr. 26, 2007, 6070-6071, 129, American Chemical Society.
Pushparaj, et al., Flexible energy storage devices based on nanocomposite paper, Proc. Natl. Acad, Sci., Aug. 15, 2007, 13574-13577, 104, PNAS.
Hernandez-Ramirez, et al., Water vapor detection with individual tin oxide nanowires, Nanotechnology, Sep. 19, 2007, 18, 424016, IOP Publishing Ltd, UK.
Yang, et al., RFID Tag and RF Structures on a Paper Substrate Using Inkjet-Printing Technology, IEEE Trans. Microwave Theory Tech., Dec. 2007, 2894-28901, 55-12, IEEE.
Kauffman, et al., Angew. Chem. Int. Ed., Jul. 18, 2008, 6550-6570, 47, Wiley-VCH GmbH & Co. KGaA, Weinheim.
Zhao, et al., Lab on paper, Lab Chip, Oct. 24, 2008, 1988-1991, The Royal Society of Chemistry.
Martins, et al., Write-erase and read paper memory transistor, Appl. Phys. Lett., Nov. 17, 2008, 203501-1-203501-3, 93, American Institute of Physics.
Nystrom, et al., Ultrafast All-Polymer Paper-Based Batteries, Nano Lett., Sep. 9, 2009, 3635-3639, 9-10, American Chemical Society.
Siegel, et al., Foldable Printed Circuit Boards on Paper Substrates, Adv. Funct. Mater., Oct. 15, 2010, 28-35, 20, Wiley-VCH Verlag GmbH & Co. KGaA, Weinheim.
Penza, et al., Metal-modified and verically aligned carbon nanotube sensors array for landfill gas monitorin . . . , Nanotechnology, Feb. 15, 2010, 21, 105501, IOP Publishgin Ltd.
Kim, et al., Paper as a Substrate for Inorganic Powder Electroluminescence Devices, IEEE Trans. Electron Devices, Sep. 2010, 1470-1474, 57-6, IEEE.
Wang, et al., Dye sensitized solar cells on paper substrates, Sol. Energy Mater. Sol. Cells, Mar. 22, 2011, 2531-2535, 95, Elsevier B.V.

* cited by examiner

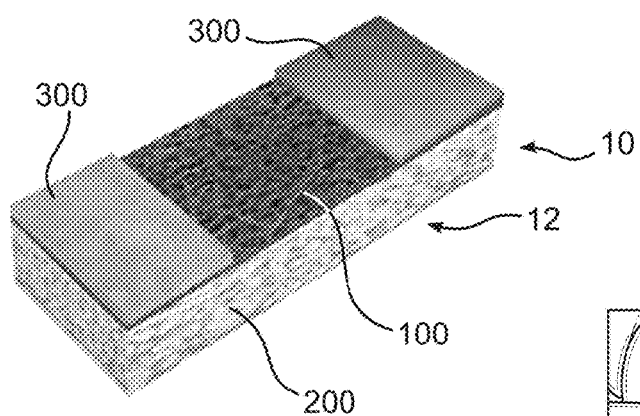
FIG. 1
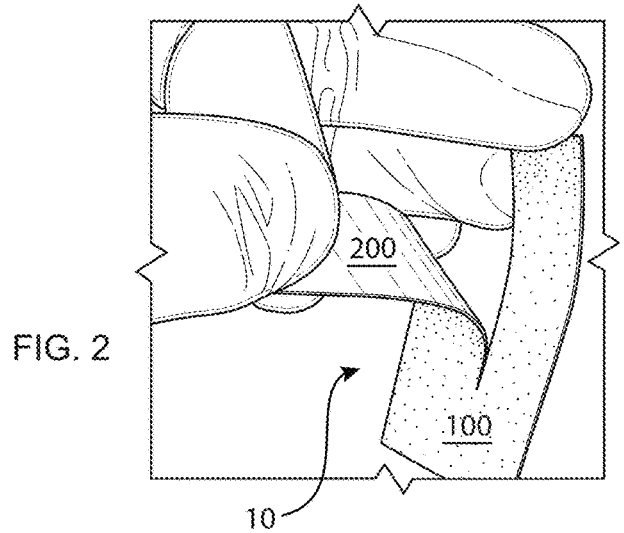
FIG. 2
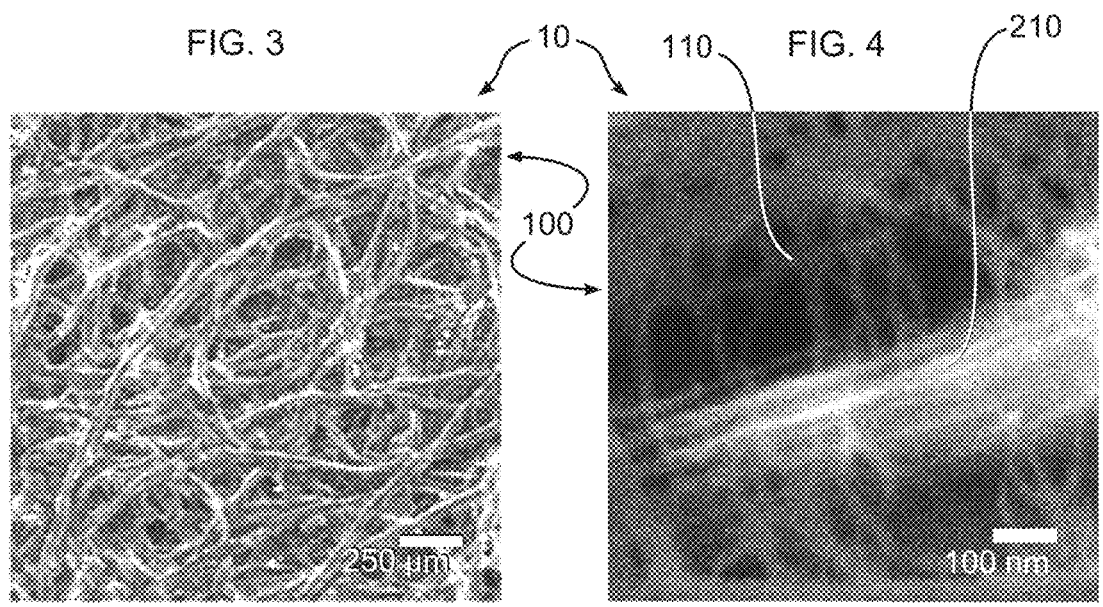
FIG. 3
FIG. 4

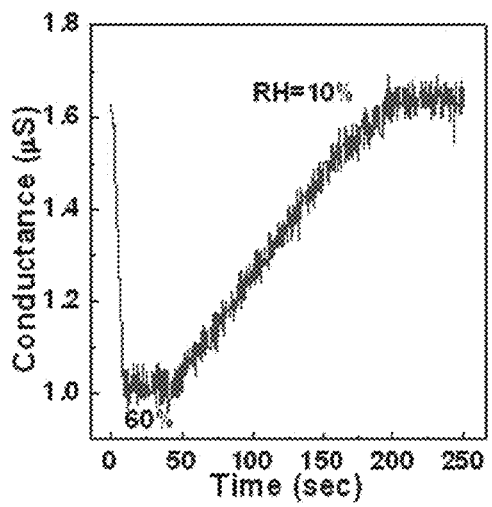
FIG. 12
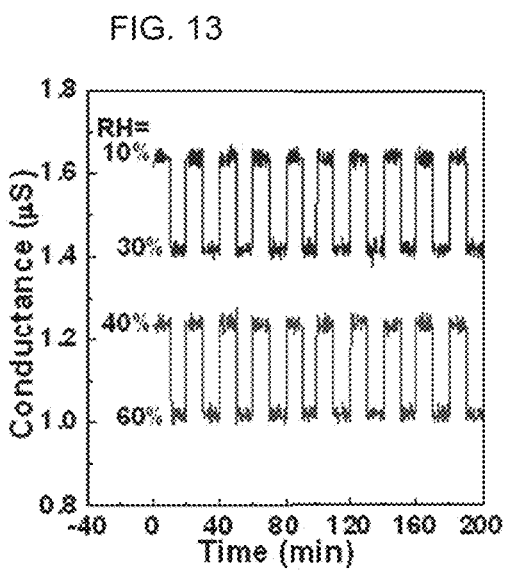
FIG. 13
FIG. 14
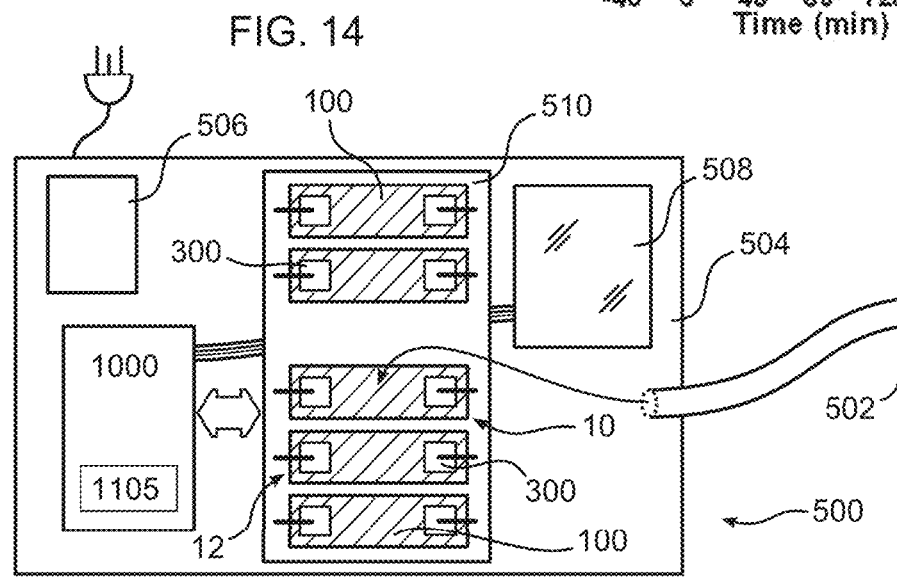

ELECTRICAL RESPONSE USING NANOTUBES ON A FIBROUS SUBSTRATE

CROSS REFERENCE TO RELATED APPLICATION

This application is a non-provisional of, and claims priority to, U.S. Provisional Patent Application Ser. No. 61/772,681 filed Mar. 5, 2013. The subject matter of the provisional application is hereby incorporated by reference in its entirety.

ORIGIN OF INVENTION

The invention described herein was made by employees of the United States Government and may be manufactured and used by or for the Government of the United States of America for governmental purposes without the payment of any royalties thereon or therefor.

BACKGROUND OF INVENTION

Technical Field of Field of the Invention

The present invention relates to electrical signals using nanostructures on a fibrous substrate, and more particularly to sensing gas or vapors using carbon nanostructures on cellulose paper.

Description of the Prior Art

Sensors are fabricated on hard substrates, such as silicon, or glass. NASA Ames Research Center has previously patented single walled carbon nanotube (SWCNT) based nanochem sensors on a silicon substrate. Electronics using paper include demonstrations of logic devices, memory, and RFID tags. Studies on paper electronics have appeared recently with implementation examples of lab-on paper, thin-film transistor, non-volatile memory, RFID tags, electroluminescence devices, dye-sensitized solar cell, battery, supercapacitor, and a printed circuit board. SWCNTs have been utilized for sensing of a wide range of gases and vapors.

SUMMARY OF THE INVENTION

In accordance with one aspect of the present invention, resistor-type humidity sensors are formed on cellulose paper, employing carboxylic acid functionalized, single walled carbon nanostructures (e.g., nanotubes, nanowires, nanoparticles) as sensing material. The sensors were solution-processed without heat and vacuum treatment. In testing one embodiment, the conductance linearly decreased with increase in the relative humidity up to 75 percent. The sensor on paper showed better sensitivity than a control sensor on glass. The cellulose-bridged charge transport between intertubes is considered to improve the moisture contact area and thus, the sensitivity of the sensor. Paper-based sensors of the disclosure are low-cost, flexible and foldable while retaining functionality, and can be fabricated with materials which are rapidly biodegradable in landfill conditions. Due to a low production cost, sensors of the disclosure can be considered disposable in that it is economic to use them a single or small number of times before disposal. Sensors of the disclosure can be formed to detect a wide variety of gases and vapors, and construction of an electronic nose can be created with an plurality of sensors.

In accordance with an embodiment of the disclosure, a device for sensing chemicals, comprises a fibrous substrate; and a plurality of carbon nanostructures intertwined within the fibrous substrate.

In various embodiments thereof, the carbon nanostructures include single walled carbon nanotubes (SWCNTs); the sensor is at least one of a capacitor-type, a transistor-type, a resistor-type, a microbalance-type, and a fiber optic-type; the sensor is functionalized; the sensor is doped; the fibrous substrate is cellulose paper; the fibrous substrate is filter paper; the fibrous substrate is porous; and the paper substrate is foldable without a loss of functionality; and the fibrous substrate is biodegradable.

In another embodiment of the disclosure, a device for producing an electrical signal in response to a stimulus comprises a flexible substrate including a layer of fibers; and a solution of dispersed carbon nanostructures coated onto and within the fibers, the solution evaporated to leave carbon nanostructures intertwined within the layer of fibers, the carbon nanostructures are functionalized by a functionalization agent.

In various embodiments thereof, the solution includes a solvent; the solution includes dimethylformamide; the functionalization agent is an acid (e.g., carboxylic acid); the carbon nanostructures are doped produce a change in an electrical signal in response to a particular stimulus; the carbon nanostructures are coated to produce a change in an electrical signal in response to a particular stimulus; the flexible substrate including a layer of fibers is porous paper; and the device further includes electrodes in contact with the intertwined carbon nano structures.

In another embodiment thereof, the device further includes a housing and a plurality of distinct ones of the flexible substrate portions coated with a solution of dispersed carbon nano structures.

In a further embodiment of the disclosure, a method for producing an electrical signal in response to a stimulus comprises providing a flexible substrate including a layer of fibers; functionalizing carbon nanostructures using a functionalization agent; pouring a solution including the functionalized carbon nanostructures onto the layer of fibers; and evaporating the solution to leave carbon nanostructures intertwined within the layer of fibers.

BRIEF DESCRIPTION OF THE DRAWINGS

The accompanying figures, where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 1 is a schematic illustration of a sensor of the disclosure, formed using a cellulose paper substrate and carbon nanostructures;

FIG. 2 is a sensor in accordance with FIG. 1, illustrating that the device can be cut, and is flexible;

FIG. 3 is an SEM image of the cellulose paper of FIG. 2;

FIG. 4 is a magnified image of the crosslinked CNTs of FIG. 3;

FIG. 12 is a graph of response and recovery curves for a change between 10 and 60 percent RH for a device in accordance with the disclosure;

FIG. 13 illustrates repeatability curves of the CNT sensor on paper of the disclosure;

FIG. 14 is a schematic illustration of an electronic "nose", incorporating sensors in accordance with the disclosure;

DETAILED DESCRIPTION OF THE INVENTION

Figure 5:
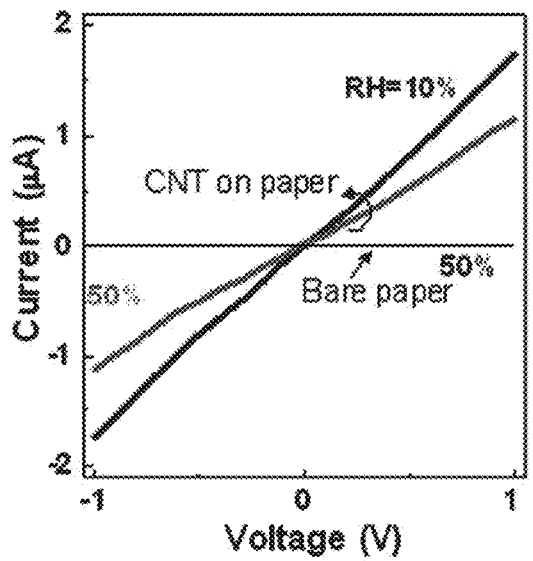
FIG. 5 is a graph of current-voltage (I-V) characteristics of bare (intrinsic) paper and a CNT resistor of the disclosure, for RH=10 percent and RH=50 percent.

It is to be understood that the disclosed embodiments disclosed herein are merely examples and that the systems and methods described below can be embodied in various forms. Therefore, specific structural and functional details disclosed herein are not to be interpreted as limiting, but merely as a basis for the claims and as a representative basis for teaching one skilled in the art to employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term "another," as used herein, is defined as at least a second or more. The terms "including" and "having," as used herein, are defined as comprising (i.e., open language). The term "coupled," as used herein, is defined as "connected," although not necessarily directly, and not necessarily mechanically.

In accordance with the disclosure, sensors on fiber or fibrous material are fabricated to identify gas or vapors (chemicals). Sensors of the disclosure can be fabricated at a lower cost, and are foldable, flexible, and biodegradable. In another embodiment, filter paper is used as a fibrous material substrate. In another embodiment, relative humidity (presence of water vapor) is measured. However, it should be understood that sensors may be fabricated in accordance with the invention to detect many different types of vapors or disbursed chemicals. Sensors of the disclosure include single walled carbon nanotubes as the sensor material, although other nanostructures may be employed. Various functionalization and doping strategies can be used to sense different chemicals (gases and vapors).

Sensor material can be formed as bulk or thin films of nanomaterials, including nanostructures, nanotubes, nanowire and/or nanoparticles. Sensor material itself can be silicon, tin oxide or other oxide, carbon nanostructures or graphene. The measured variable can be resistance (inverse of conductance), capacitance, dielectric constant or any other easily measurable physical property. In accordance with the disclosure, single walled carbon nanotubes (SWCNTs) are deposited on paper substrate to enable cheaper, flexible, and if needed, economically disposable sensors. While single walled carbon nanotubes are described in detail herein, it should be understood that, alternatively, multi-walled carbon nanotubes (MWCNTs), as well as graphene, can be effectively utilized.

Gas sensors can be classified according to transduction method; for example, capacitor, transistor, resistor, microbalance, and fiber optic. Each class has its different strengths and weaknesses, but the resistive type sensor is characterized by its simple structure, low fabrication cost, and simple associated read-out circuitry.

Accordingly, herein, a resistor type sensor has a network of cross linked SWCNTs, for example, with purity over 99 percent, although greater or lesser purity can be provided, with acceptable results. A readily available cellulose paper, for example used for filtration, is employed as a substrate. In one embodiment, the filter paper exhibits medium porosity with a flow rate of 60 mL/min, and a particle retention of 5-10 μm. A high roughness and porosity of a paper is useful in accordance with the disclosure, because these properties can increase a contact area with ambient air, thereby promoting adhesion or contact of measured material to the CNTs.

While paper is described as a substrate in examples herein, it should be understood that other fibrous materials can be used together with carbon nanostructures to form sensors, as described herein. These materials can include natural or synthesized fibrous material, including plant fibers, fibers from animals, silks, polymeric fibers, photo-paper, and nanocellulose paper. It should be understood, however, that fibrous materials exhibiting substantially different conductivity compared with cellulosic fibers would produce substantially different results, which may or may not be advantageous. Likewise, a relative change in fiber length and/or width, as compared to cellulosic fibers, can result in a different distribution of CNTs, with results varying depending on an extent of, for example, intertwining and adhesion between the CNTs and fibers. In addition, fibers can be optionally combined with a backing for a desired extent of flexibility or strength of the sensor.

Devices of the disclosure may be fabricated and implemented without heat treatment or vacuum environment. The SWCNTs were functionalized with carboxylic acid (COOH), rendering them hydrophilic, thereby increasing adhesion with the substrate. The functionalized SWCNTs were initially dispersed in dimethylformamide solution. Other dispersing agents can be used, including for example water or other materials which are not deleterious to the substrate or nanostructures. Additionally, a surfactant can be used, including for example dodecylbenezenesulfonate (DDBS), to improve dispersion of the SWCNTs.

The film, composed of networks of cross linked CNTs, was formed using drop-cast coating followed by evaporation of the solvent. Ten cm filter paper was conformally coated with COOH-functionalized SWCNTs. The resulting flexible paper can be custom cut to any size or shape. Imaging results show that the nanoscale CNTs are firmly entangled with the microscale cellulose fibers. Adhesive copper foil tape was used for contact electrodes and the distance between the two electrodes was about 2 mm. This distance can be adjusted to any desirable length, and other materials may be used for electrodes.

Any of a wide variety of functionalization agents can be used, as currently known, or hereinafter discovered. A particular functionalization agent is selected for optimizing a change in resistivity, or other measurable characteristic of nanostructures on a fibrous substrate in accordance with the disclosure, for detecting a particular gas or substance. Alternative functionalization agents can include, for example, doping agents, metal loading, or the attachment of other molecular groups.

The disclosure provides an electrical/electronic gas or vapor sensor with a paper substrate. Sensors of the disclosure are relatively easy to fabricate compared to prior art sensors, and do not require heating or vacuum treatment. Further, sensors of the disclosure may be fabricated using simple solution processing, at a lower cost than prior art sensors. Additionally, sensors of the disclosure are foldable and flexible, and can be fabricated with materials that readily biodegrade in weeks or months, rather than in years, in landfill conditions.

Devices in accordance with the disclosure can be used to detect a wide variety of gases and vapors through the use of carbon nanostructures that are functionalized, doped or coated to enable each particular gas/vapor or combination of gases and vapors. As such, devices of the disclosure form a key component of a versatile 'electronic nose' device, with applications wherever chemical (gas/vapor) sensors are used, including but not limited to industrial, mining, security, biomedical, food processing, agricultural and other applications. Additionally, devices of the disclosure have a relatively low weight compared with respect to prior art sensors, and can also function using relatively less power.

In accordance with the disclosure, a humidity sensor on cellulose paper is fabricated using single-walled carbon nanotubes functionalized with carboxylic acid. The conductance shift of the nanostructures network entangled on microfibril cellulose is utilized for humidity sensing. Compared to a control sensor made on a glass substrate using prior art technology, the nanostructure network and cellulose-mediated charge transport on the paper substrate work together to enhance sensitivity. In a test embodiment, a sensor of the disclosure exhibited linear conductance shift up to a relative humidity of 75 percent with good repeatability and low hysteresis. It is expected that a broader range of operation would be possible, with further development.

A circuit model can be used to explain the sensor results. Additionally, the sensor application can be extended to other gases and vapors, and to the construction of an electronic nose with one or more sensors, each sensing one or more gases, for example, in an array of sensors. Methods of the disclosure can be used to construct a wide variety of paper electronics, useful particularly for low-cost, low weight, single or limited use/disposable applications.

Electronic devices built on cellulose paper substrates, using methods of the disclosure, can be cheaper than an equivalent class of functionality provided by solid-state devices of the prior art, while providing reasonable or improved performance. Further, paper-based devices of the disclosure can additionally be used for flexible, foldable, biodegradable, and disposable applications such as biosensors, intelligent packaging, business cards, and advertising banners.

Chemical and biosensors on inexpensive substrates such as paper, constructed in accordance with the disclosure, are useful because their utility covers a wide range of applications. In the present disclosure, a humidity sensor is built on a paper substrate, illustrating a fundamental building block of paper electronics. Performance metrics, including linearity, sensitivity, hysteresis, and response/recovery times were assessed for an embodiment. Single-walled carbon nanotubes (SWCNTs) were used to construct the sensor on paper. Prior art silicon, polymer, or organic conducting materials were not used.

Gas sensors can be classified according to transduction method into capacitor transistor, resistor, microbalance, and fiber optic. Each class has its own strengths and weaknesses, but the resistive type sensors are characterized by their simple structure, low fabrication cost, and simple read-out circuitry. Here, a resistor type humidity sensor was fabricated on cellulose papers.

With reference to FIGS. 1-4, a sensor 10 including a network of crosslinked SWCNTs 100 is illustrated, for example, with a purity over 99 percent, although lower or higher purity can be effectively used. Paper is used as a substrate 200. In this embodiment, readily available cellulose filter paper was selected, which has a medium porosity with a flow rate of 60 mL/min and particle retention of 5-10 nm, although different porosity and flow rates can be effectively utilized. Without being bound to any particular theory, it is considered that the roughness and porosity of the paper provides an increased contact area with ambient air containing the gas or vapor, and additionally promotes adhesion of CNTs.

No heat treatment or vacuum environment were involved in the course of device processing. The SWCNTs were functionalized with carboxylic acid (COOH) to render them hydrophilic, thus increasing the adhesion with the substrate. The functionalized SWCNTs were dispersed in dimethylformamide solution. The film composed of networks of crosslinked SWCNTs 100 was formed using drop-cast coating followed by evaporation of the solvent.

Adhesive copper foil tape was used for contact electrodes 300 (FIG. 1) and the distance between the two electrodes, in an embodiment, was about 2 mm, although substantially smaller or larger separation is possible, as would be understood by a skilled practitioner. The 10 cm filter paper 200 was conformally coated with COOH-functionalized SWCNTs 100, after which the paper remains flexible, and can be cut to a desired shape, as shown in FIG. 2.

In this embodiment, the substrate was cut to a size of 2 by 10 mm. With reference to FIGS. 3 and 4, scanning electron microscopy (SEM) images depict that the nanoscale CNTs 110 are firmly entangled with the microscale cellulose fibers 210.

The current-voltage (I-V) characteristics were measured using a semiconductor parameter analyzer (Agilent 4156C). The sensors were tested within a thermostatic test chamber. The relative humidity (RH) of the test chamber was controlled by mixing appropriate amounts of dry and wet air. Testing was carried out as the relative humidity varied from 10 to 90 percent, while the temperature of the chamber was maintained at room temperature.

FIG. 5 illustrates the I-V characteristics of the bare paper substrate 200 (FIG. 1), and an embodiment of a sensor 10 forming a CNT resistor 12, under conditions of relative humidity RH=10 percent and RH=50 percent. Measured electrical current was zero on the unprocessed paper substrate 200, suggesting that the cellulose network is an insulator. CNT resistors show Ohmic characteristics and the conductance decreases with increasing moisture content. Because the differential resistance is constant over the supply voltages, the sensitivity is identical regardless of the operation bias. In other words, a low voltage operation does not hinder the sensitivity, thus allowing low power operation. This low power feature is important in self-powered applications such as ubiquitous sensor nodes. The operation voltage in this application is fixed at 1 Volt.

Figure 6:
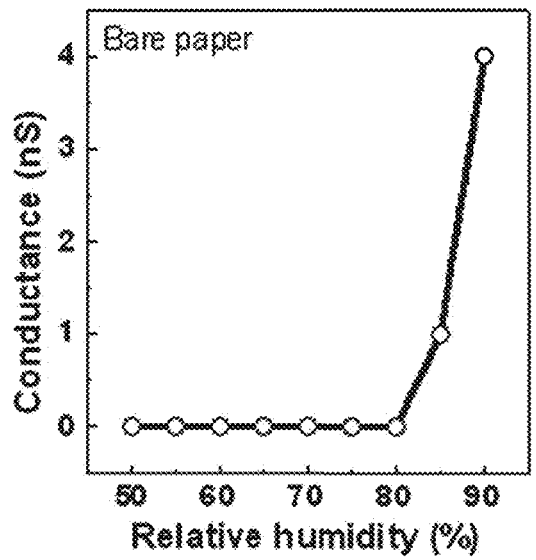
FIG. 6 is a graph of conductance responses of bare cellulose paper substrate.

To clarify the impact on the paper substrate 200 with respect to humidity, bare cellulose paper was tested first (FIGS. 5 and 6). When the relative humidity is very high, water dissociation occurs on the moist cellulose fiber under the applied bias, creating H$^+$ and OH$^-$ ions. Thus, the electrical charges can flow due to ionic conduction. FIG. 6 illustrates the threshold humidity, defined as an RH value that initiates the current conduction for bare paper. The bare paper substrate acts as an insulator under low RH but current becomes non-zero at high RH, above about 85 percent. The intrinsic paper may therefore be used as a threshold humidity detector, but it is thus impractical for most sensor applications.

Figure 7:
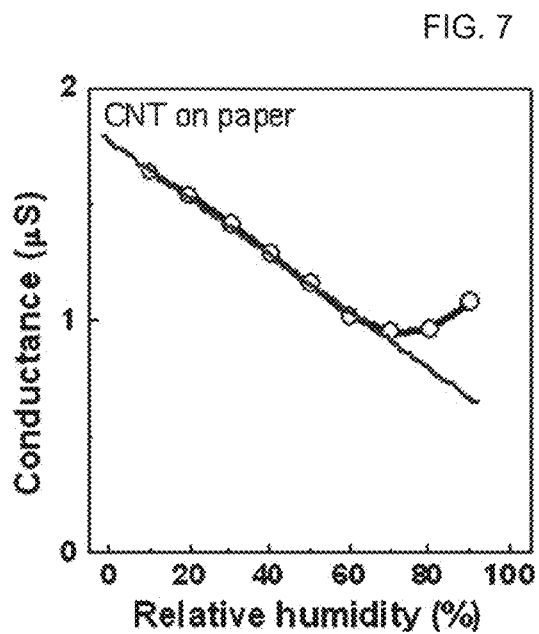
FIG. 7 is a graph of conductance responses of a CNT sensor on cellulose paper substrate of the disclosure.
Figure 8:
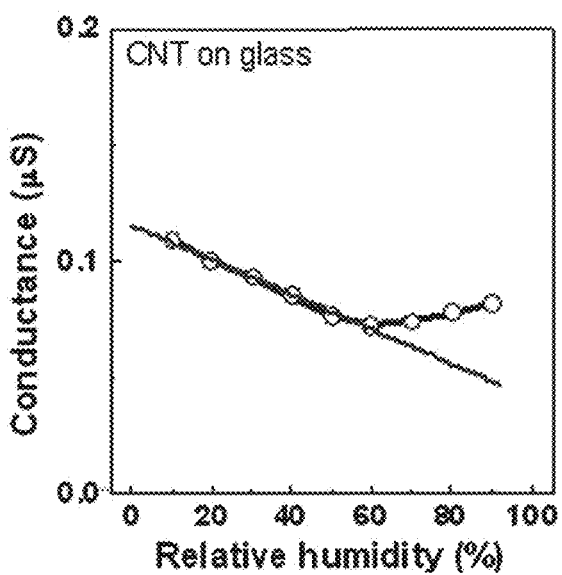
FIG. 8 is a graph of conductance for a CNT sensor on a glass substrate.

In contrast, the CNT resistor sensor 12 responds over most of the range of RH as shown in FIGS. 7 and 8. The conductance decreases linearly with increasing humidity up to about RH=75 percent, and then increases slightly with humidity. The sensitivity is defined as the ratio of the relative conductance difference over the relative humidity difference: [(Sx−S0)/S0]/(RHx−RH0) where the subscripts x and 0 correspond to specific RH values under investigation and RH=0 respectively. The sensitivity is 6 percent in the linear regime in FIG. 7.

Certain effects of humidity on electrical conductivity of CNTs are known. Without being bound by any particular theory in the instant disclosure, it has been proposed that the CNT network shows global p-type semiconducting behavior, where the electrical conduction is dominated by holes. The H2O molecules adsorbed on the surface are known to behave as electron donors. Accordingly, an increase in humidity results in a reduction of hole density of the p-type nanostructures. In addition to the electron donation model, other mechanisms for the humidity effect have been proposed as well: hydrogen bonding on the oxygen defect sites present on the nanostructures; and possible introduction of charge traps on the nanostructures, arising from direct adsorption of water molecules on the substrate.

In any case, the conductance decrease for RH greater than 75 percent observed in these tests appears to be canceled out by some factors. If the conduction via cellulose fibers is attributed to this offset, the transition should occur around RH=85 percent. However, the observed transition point is smaller than the threshold humidity of the bare cellulose, which implies presence of some other mechanism. This inference is reasonable, due to the fact that the conductance increase of bare paper is of the order of nS, whereas the conductance decrease of CNT resistor 12 is of the order of μS. Again, without being bound to any particular theory, a possible cause of compensation is a counter doping effect. Because the H$_2$O molecules act as electron donors, the p-type CNT can become an extrinsic n-type semiconductor, when the ambient humidity reaches a certain level. After compensation, the conductance of n-type sensors increases with humidity, and the trend offset therefore can be explained by the counter doping effect.

Figure 9:
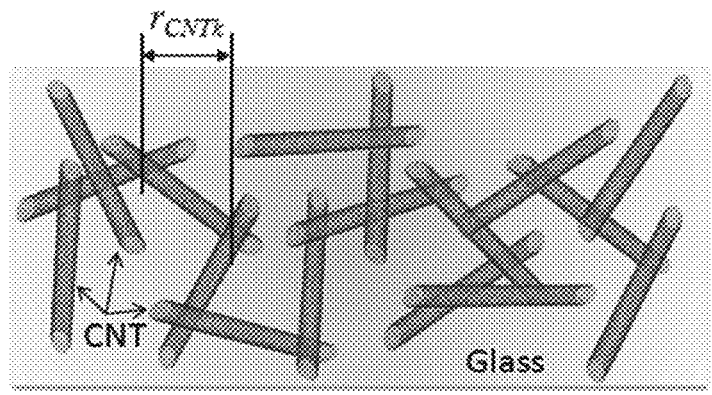
FIG. 9 is a schematic illustration of a CNTs on a glass substrate.
Figure 10:
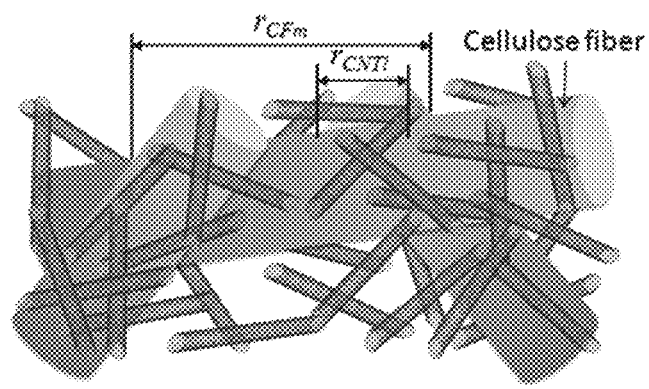
FIG. 10 is a schematic illustration of a CNT sensor on cellulose paper substrate in accordance with the disclosure.

To compare the sensing performance between devices built on different substrates, some control sensors were fabricated on glass using an identical process. The paper device exhibits superior sensitivity relative to glass sensitivity, as shown in FIG. 8. At RH=10 percent, the conductance of the sensor on glass is roughly one order of magnitude lower than that on paper. The porous and rough surface of the paper is favorable to accommodate individual CNTs tightly compared to the relatively uniform and even surface of the glass (FIG. 9). Furthermore, the paper can soak up CNTs from the suspension solution due to high wettability of the paper, leading to firm adhesion (FIG. 10). As a result, the connectivity of SWCNTs is promoted easily on paper. The sensitivity of the sensor-on-glass is 1 percent in the linear regime and thus, the paper sensor displays significantly higher sensitivity than the glass sensor.

Figure 11:
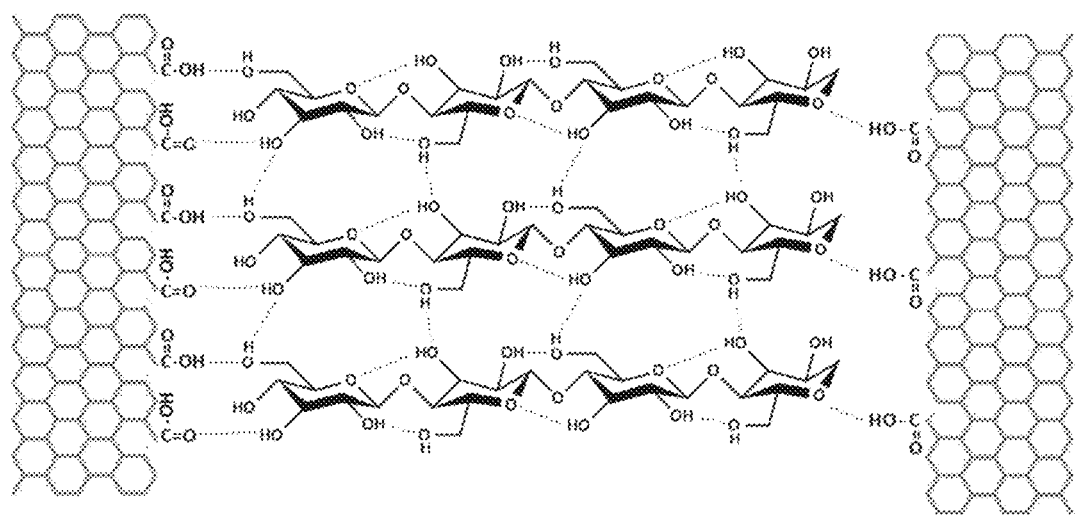
FIG. 11 is a schematic illustration of carrier conduction between unconnected nanostructures assisted by cellulose fiber, in accordance with the disclosure.

In one possible explanation of the observed results, a simplified circuit model is presented, and a schematic of the conduction mechanism is shown in FIG. 11. In FIG. 9, the CNTs are randomly networked on glass, whereas in FIG. 10, the CNTs are entwined with the cellulose fibers as a backbone of the paper. On glass, the current pathway is formed only across CNTs. The overall resistance on glass ($R_{Glass}$) is composed of n resistances of k$^{th}$ CNT ($r_{CNTk}$) in series:

$$R_{Glass} = r_{CNT1} + r_{CNT2} + \ldots + r_{CNTk} \qquad (1)$$

On cellulose, and with reference to FIGS. 10-11, the current pathways are formed by nanoscale CNTs and by microscale cellulose fibers. Therefore, the overall resistance on paper ($R_{Paper}$) is considered to be a parallel combination of the resistance via CNTs ($R_{CNT}$), the resistance of cellulose fibers ($R_{CF}$), and the resistance through CNTs and cellulose fibers ($R_{CNT,CF}$).

$$\frac{1}{R_{Paper}} = \frac{1}{R_{CNT}} + \frac{1}{R_{CF}} + \frac{1}{R_{CNT,CF}} \qquad (2)$$

$$R_{CNT} = r_{CNT1} + r_{CNT2} + \ldots + r_{CNTl-1} + r_{CNTl}$$

$$R_{CF} = r_{CF1} + r_{CF2} + \ldots + r_{CFm-1} + r_{CFm}$$

$$R_{CNT,CF} = r_{CNT1,CF1} + r_{CNT,CF2} + \ldots + r_{CNT,CFn-1} + r_{CNT,CFn}$$

$R_{CNT}$ is composed of l resistances of l$^{th}$ CNT ($r_{CNTl}$) in series, which is similar in form as $R_{Glass}$. However, $R_{CNT}$ is smaller than $R_{Glass}$, because CNTs are closely and densely packed as previously deduced. The $R_{CF}$ is composed of m resistances of m$^{th}$ microfibril cellulose ($R_{CFm}$) in series, but its contribution to RCF can be neglected because the global cellulose fiber network tends to be insulating. However, the localized cellulose fibers segmented by CNTs can significantly impact $R_{Paper}$. The $R_{CNT,CF}$ is the total sum of the localized resistance of n$^{th}$ cellulose fibers ($r_{CNT,CFn}$) segmented by CNTs. The cellulose is a straight chain polymer with rod-like conformation. The cellulose molecules have multiple hydroxyl groups that form hydrogen bonds within and between cellulose molecules. In addition, these hydroxyl groups can also connect to the surface of CNTs by hydrogen bonding. Therefore, although the microfibril fiber is an insulator, these segments electrically bridge the adjacent disconnected CNTs. Then, carrier hopping and tunneling, which boost inter-tube conduction, can take place. As a result, there is an increase in percolation path, and a reduction of the effective conduction distance results in the sensitivity increase.

FIG. 12 shows the response and recovery curves of a sensor 10 having the form of CNT resistor 12. At t=0, the sensor in an ambient environment of 10 percent RH is exposed to 60 percent RH air, and then switched back to 10 percent RH. The sensor response time is about 6 sec and the sensor recovery time to reach 95 percent of the final state is about 120 sec. FIG. 13 shows the good repeatability of the sensor when alternatively exposed to different humidity levels. The dynamic response shows that the conductance at a given humidity is identical, implying a negligible hysteresis effect. Finally, the performance of paper-based sensors of the disclosure, including CNT resistor sensor 12, is comparable to other published CNT-based humidity sensors on various substrates. For example, MWCNTs modified with $MnWO_4$ show a sensitivity of about 8 but very high response and recovery times. In contrast, $LiClO_4$/MWCNTs show a higher sensitivity and a modest recovery time of 1 min. Response and recovery times of 30 sec and 25 sec respectively have been obtained for switching between 8 and 93 percent RH for PMMA/MWCNT thin films doped with KOH. Compared to resistive sensors, field effect transistor sensors with CNTs appear to provide msec response times. Sensors of the disclosure also perform better than oxide nanowire-based humidity sensors in terms of sensitivity and response/recovery times, besides room temperature operation.

With reference to FIG. 14, a gas/vapor analyzer 500, in a simple form, includes a gas capture inlet 502, a housing 504, at least one sensor 10, a power supply 506, and a display 508. Gas or vapor enters inlet 502, where it is passed within the housing to admit the gas to the crosslinked SWCNTs 100 of one or more sensors 10, having electrodes 300. In an embodiment, a plurality of sensors 10 is configured to detect the same or different gases or vapors, or different concentrations of the same gases or vapors. In a further embodiment, the sensors are isolated from each other, and the gas or vapor may be selectively passed to one or more sensors 10 or sensor groups.

A processing board, for example an analog to digital or A/D board 510 can be provided, configured to convert resistance or conductance through sensor 10 into a digital signal understood by computer system 1000. After processing, a result of analysis can be provided to an operator of analyzer 500, for example upon a display 508, or transmitted or transcribed through other known means. In the absence of computer system 1000, resistance signals may be displayed by any known means, including for example a meter display.

A resistor CNT 12 optimized for measuring humidity has been described above, and one or more resistors CNT 12 may be provided within analyzer 500. In addition, as described above, various other forms of CNT detectors may be fabricated upon paper as described herein, providing for sensing of any of a wide variety of gases or vapors. For example, in addition to the SWCNTs illustrated herein, one or more of the following sensors can be provided: MWCNTs modified with $MnWO_4$; $LiClO_4$/MWCNTs; PMMA/MWCNT thin films doped with KOH. These sensors can be prepared in the manner described above for SWCNTs. In this manner, (a) different materials may be sensed, and or (b) different sensing attributes may be exploited, for example response times and sensitivity, to provide more useful results.

Software, executable upon system 1000, can be configured to synthesize results from, for example a fast response time sensor with lower sensitivity, with a slower response time sensor with higher sensitivity. For gases or vapors not related to water, a strategy must be employed to elicit a targeted signal, including modifying the nanostructure on fibrous material, as described herein, with dopants, metal particles, and other functionalization agents. Alternatively, nanoparticles or nanowires of inorganic materials may also be used as the sensing component, provided they elicit a measurable response.

While a resistive sensor is detailed herein, it should be understood that other known and hereinafter developed forms of nanostructure devices can be fabricated in accordance with the disclosure, including for example devices which are made from the following types of nanostructures: capacitor, transistor, microbalance, and fiber optic. More specifically, these types of nanostructures may be combined with a fibrous substrate using the techniques described herein, to form sensing, electronic, optical, and other types of devices, including for example capacitive sensors and thin film transistors.

Further, in addition to vapors, liquids, semi-liquids, or solid samples may be placed in contact with sensors 10 of the disclosure to sense the contents or other physical attributes of the sample.

Exemplary Computer System

Figure 15:
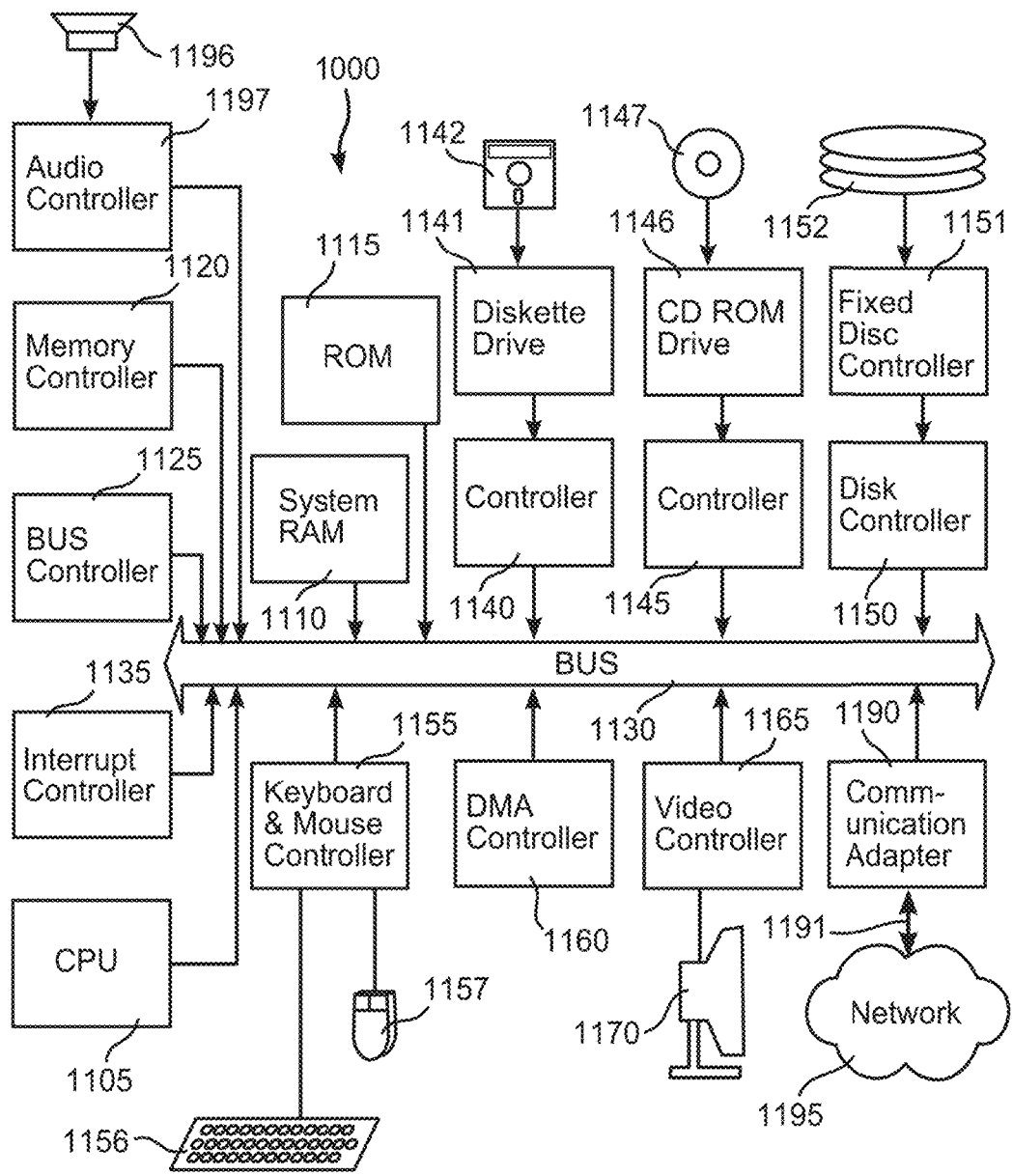
FIG. 15 is a diagram of a computer system, some or all of which may be used together with sensors of the disclosure.

FIG. 15 illustrates the system architecture for a computer system 1000 such as a server, work station, embedded system, gas/vapor analyzer system, or other processor on which the disclosure may be implemented. The exemplary computer system of FIG. 15 is for descriptive purposes only. Although the description may refer to terms commonly used in describing particular computer systems, the description and concepts equally apply to other systems, including systems having architectures dissimilar to FIG. 15.

Computer system 1000 includes at least one central processing unit (CPU) 1105, or server, which may be implemented with a conventional microprocessor, a random access memory (RAM) 1110 for temporary storage of information, and a read only memory (ROM) 1115 for permanent storage of information. A memory controller 1120 is provided for controlling RAM 1110.

A bus 1130 interconnects the components of computer system 1000. A bus controller 1125 is provided for controlling bus 1130. An interrupt controller 1135 is used for receiving and processing various interrupt signals from the system components.

Mass storage may be provided by diskette 1142, CD or DVD ROM 1147, flash or rotating hard disk drive 1152. Data and software may be exchanged with computer system 1000 via removable media such as diskette 1142 and CD ROM 1147. Diskette 1142 is insertable into diskette drive 1141 which is, in turn, connected to bus 1130 by a controller 1140. Similarly, CD ROM 1147 is insertable into CD ROM drive 1146 which is, in turn, connected to bus 1130 by controller 1145. Hard disk 1152 is part of a fixed disk drive 1151 which is connected to bus 1130 by controller 1150. It should be understood that other storage, peripheral, and computer processing means may be developed in the future, which may advantageously be used with the disclosure.

User input to computer system 1000 may be provided by a number of devices. For example, a keyboard 1156 and mouse 1157 are connected to bus 1130 by controller 1155. An audio transducer 1196, which may act as both a microphone and a speaker, is connected to bus 1130 by audio controller 1197, as illustrated. It will be obvious to those reasonably skilled in the art that other input devices, such as a pen and/or tablet, Personal Digital Assistant (PDA), mobile/cellular phone and other devices, may be connected to bus 1130 and an appropriate controller and software, as required. DMA controller 1160 is provided for performing direct memory access to RAM 1110. A visual display is generated by video controller 1165 which controls video display 1170. Computer system 1000 also includes a communications adapter 1190 which allows the system to be interconnected to a local area network (LAN) or a wide area network (WAN), schematically illustrated by bus 1191 and network 1195.

Operation of computer system 1000 is generally controlled and coordinated by operating system software, such as *nix, or a Windows system, commercially available from Microsoft Corp., Redmond, Wash. The operating system controls allocation of system resources and performs tasks such as processing scheduling, memory management, networking, and I/O services, among other things. In particular, an operating system resident in system memory and running on CPU 1105 coordinates the operation of the other elements of computer system 1000. The present disclosure may be implemented with any number of commercially available operating systems.

One or more applications, such as an HTML page server, or a commercially available communication application, may execute under the control of the operating system, operable to convey information to a user.

Study of Effect of Relative Humidity on Ammonia.

A comparative study has been conducted of response to exposure of several functionalized carbon nanotube-based (CNT-based) sensors to fluids containing ammonia fluids. The CNT sensors include an electrical circuit that allows measurement of changes in an electrical parameter value (EPV, including electrical current, voltage, resistance, impedance, conductance, inductance. etc.). A first group of CNT sensors includes sensors deposited directly on a paper substrate, with the CNTs settling into or onto various layers of the (porous) paper. A second group of CNT sensors comprises nanoscale CNTs deposited on microscale cellulose fibers, as a substrate. Conventional substrates have included plastic, glass and silicon. An increase in $NH_3$ concentration is often associated with kidney disorders and/or development of ulcers. The Occupational Safety and Health Administration has issued $NH_3$ exposure guidelines of 25 ppm and 35 ppm for 8 hours exposure and 15 minutes exposure, respectively.

Some types of devices are not suitable for use in $NH_3$ sensing. For example, metal-oxide semiconductors work only at relatively high temperatures, such as T=150° C., which is unsuitable for paper substrates.

In this study, a concentration range of 10-100 ppm $NH_3$ was considered. The first group of sensors was prepared by a CNT drop-coating procedure to produce a layer-by-layer structure on a 10 cm square filter paper. The second group of sensors was produced by filtering on a CNT-cellulose composite film, using ordinary papermaking processes. Single wall CNTs were used for both groups. A sensor is placed in a chamber with electrical feed-through. A DC current of 10 μAmps was applied, and the induced DC voltage was measured, as a direct or indirect measurement of resistance or conductance. A measured voltage of 10 Volts may produce a resistance of about 1 MegOhm. Concentration of $NH_3$ is controlled by mixing dry $NH_3$ and dry air. Dry air was also used to flush substances already absorbed from the CNT. Relative humidity (RH) and temperature adjacent to the sensors were controlled at RH=30 percent and T=25° C., respectively.

The CNTs offer an abundance of reaction sites. When $NH_3$ molecules are adsorbed on the surface, these molecules donate electrons to the CNTs, which usually behave as p-type semiconductors with holes as majority carriers. Donation of electrons reduces the hole population and increases the system resistance R.

Figure 17:
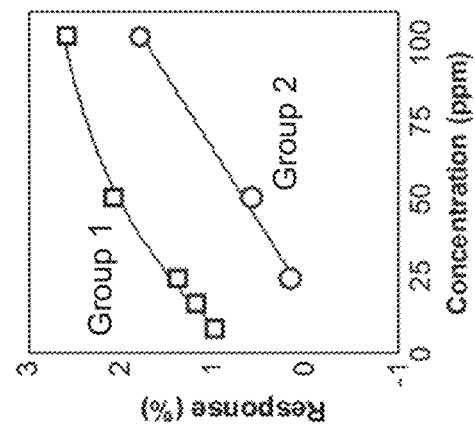
FIGS. 16 and 17 graphically illustrate EPV response, as a function of time and of $NH_3$ concentration.
Figure 16:
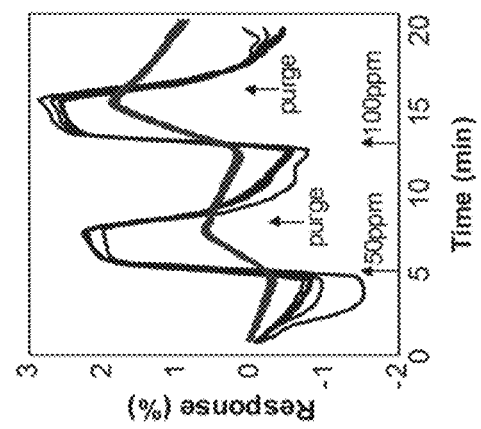
Figure 18:
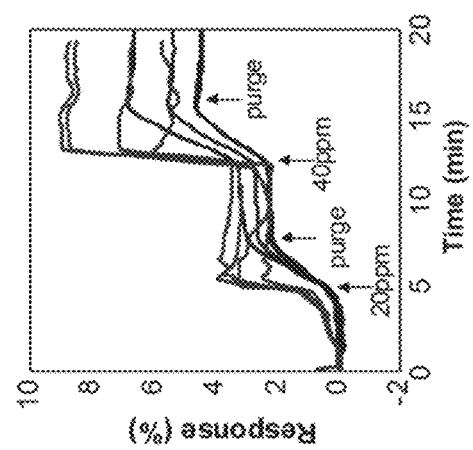
FIG. 18 graphically illustrates EPV response and EPV recovery for cellulose-CNT composite and for bare paper.

FIGS. 16 and 17 graphically illustrate the EPV response, as a function time and as a function of $NH_3$ concentration, respectively, for exemplars in the first and second groups of sensors. The EPV response of interest here is defined as $$\Delta EPV(\kappa;NH_3)=(R(\kappa)-R0)/R0, \quad (3)$$

where R0 is initial resistance before $NH_3$ exposure, and ΔEPV often ranges from −2 percent to +3 percent for reasonable values of $NH_3$ concentration κ. An initial decease in resistance R occurs during sensor conditioning or because of surface desorption of moisture and concomitant increase in hole population. The composite cellulose response increases linearly with $NH_3$ concentration κ, and the paper response appears to saturate at relatively high $NH_3$ concentration (κ>50 ppm). From the results presented in FIG. 18, the second group of sensors (cellulose-CNT composite) appears to be less sensitive to presence of $NH_3$ than is the first group of sensors. The lower $NH_3$ sensitivity for the second group may be due, in part, to a larger fraction of CNTs being enclosed within the cellulose matrix.

In the first group, the CNTs have a larger surface reaction area. Tube-to-tube charge transport can be hindered as the volume density of CNTs in a cellulose composite becomes smaller. However, cellulose fibers, segmented and supplemented by CNTs, can contribute positively to inter-tube charge transport, through formation of hydrogen bonds between cellulose molecules and adjacent CNTs. Most of the hydroxyl groups in cellulose remain on or near the surface, which can increase charge transport in a CNT network, upon exposure to $NH_3$.

For some gases and vapors, a relatively slow sensor recovery is observed, with recovery times of several minutes. These recovery times are generally lower for a more porous substrate, such as paper, and can be reduced by supplementing the sensor ambient environment with heating, in a vacuum, or with ultraviolet irradiation.

Figure 19:
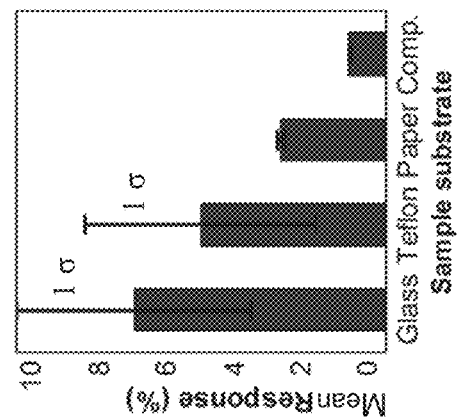
FIG. 19 graphically illustrates mean (μ) and standard deviation (1σ) of EPV response to $NH_3$ for glass, Teflon, paper, and cellulose-CNT composite substrates.
Figure 21:
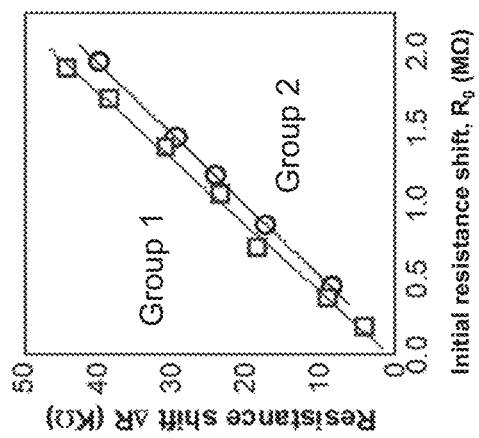
FIGS. 20 and 21 graphically illustrate shift of initial resistance values (in kiloOhms) for exposure of paper and of cellulose-CNT composite to 50 ppm of $NH_3$.
Figure 20:
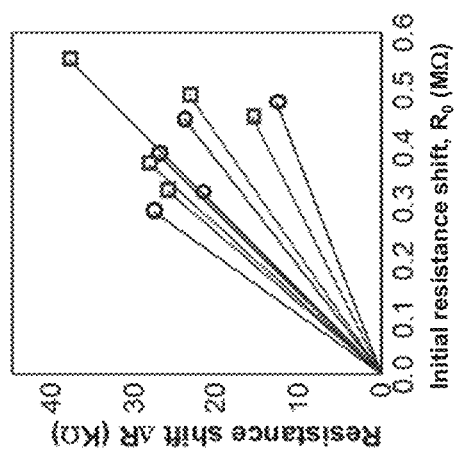

FIG. 19 graphically compares EPV responses (mean value μ and standard deviation 1σ) for $NH_3$ exposure of glass, Teflon, paper and cellulose-CNT composite. Although glass and Teflon manifest greater $NH_3$ sensitivity, the associated 1σ value for glass and for Teflon is about two-thirds of the corresponding mean value, while the associated 1σ values for paper and for cellulose-CNT composite is at most a few percent of the corresponding mean values. This indicates that, for exposure to $NH_3$, the normalized statistical fluctuation values 1σ/μ for paper and for cellulose-CNT composite are quite small, compared to the normalized statistical fluctuation values for glass and for Teflon. The normalized statistical fluctuation 1σ/μ of the response ΔEPV, as defined in Eq. (3), may arise from variation in the initially measured resistance value R0 and/or from the measured resistance value R, after exposure to $NH_3$. This is confirmed graphically in FIGS. 20 and 21, which present measured R0 values and measured EPV change values ΔR=R−R0 for a concentration value K=50 ppm of $NH_3$ for group 1 and group 2. The measured EPV responses to exposure to $NH_3$, using a paper or cellulose-CNT composite substrate, appear to be more reliable than the measured EPV response to exposure to $NH_3$, on a plurality of glass or Teflon substrates.

Figure 22:
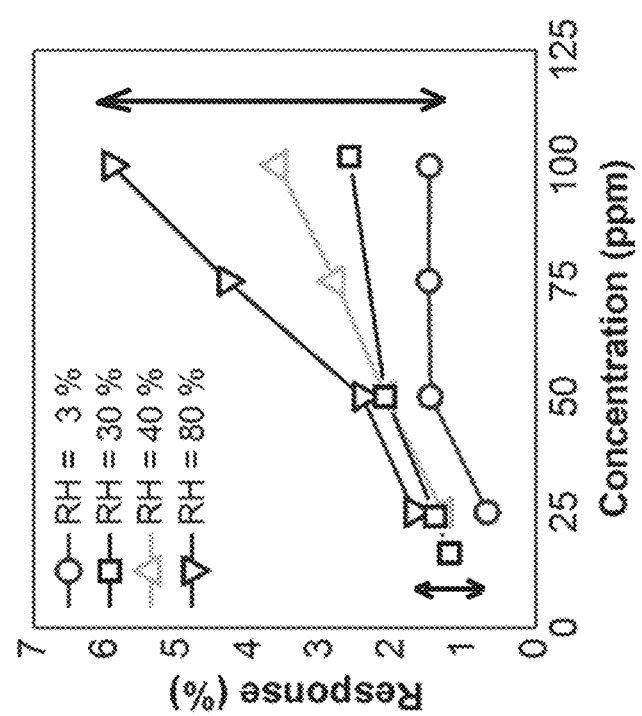
FIG. 22 graphically illustrates EPV response versus $NH_3$ concentration for RH values of 3, 30, 40 and 80 percent.

Variation of $\Delta EPV(\kappa;NH_3)$ versus concentration κ in the presence of variable relative humidity RH is complex and often produces a monotonic, but nonlinear, increase in ΔEPV with increasing RH value, as illustrated in FIG. 22. The relative humidity was maintained constant for each of four values, RH=3 percent, 30 percent, 40 percent and 80 percent. For higher RH values (30, 40 and 80 percent), the responses $\Delta EPV(\kappa;NH_3)$ versus κ tend to coalesce for concentration values κ below 50 ppm.

Variation of $\Delta EPV(\kappa;NO_2)$ with increasing RH values is also monotonic but varies substantially linearly with RH. It is preferable to provide another sensor that independently measures relative humidity RH and to use these RH measurements to appropriately modify the predicted responses $\Delta EPV(\kappa;NH_3)$ versus $\kappa$.

Non-Limiting Examples.

Although specific embodiments of the subject matter have been disclosed, those having ordinary skill in the art will understand that changes can be made to the specific embodiments without departing from the spirit and scope of the disclosed subject matter. The scope of the disclosure is not to be restricted, therefore, to the specific embodiments, and it is intended that the appended claims cover any and all such applications, modifications, and embodiments within the scope of the present disclosure.

What is claimed is:

1. A system for estimating humidity present in a gas or vapor in a specified volume, the system comprising:
    a fibrous substrate that is functionalized with at least one selected functionalizing substance, said substrate having a layer of fibers;
    a plurality of carbon nanostructures that are intertwined with the layer of fibers in the substrate;
    an electrical parameter value (EPV) measurement mechanism (EPVMM) that is electrically connected to the substrate at two or more spaced apart locations and that provides a measured EPV value that characterizes an electrical path between the two or more spaced apart locations;
    a gas admission mechanism that exposes the substrate to a known gas or vapor that has an associated relative humidity value (RH) that is not yet known; and
    a processor that receives a measured EPV for the known gas or vapor and that provides an estimate of relative humidity value of the known gas or vapor that corresponds to the measured EPV.

2. The system of claim 1, wherein said nanostructures comprise single wall nanotubes and multi-wall nanotubes.

3. The system of claim 1, wherein said fibrous substrate comprises at least one of cellulose paper, filter paper, porous paper, and biodegradable paper.

4. The system of claim 1, wherein said substrate is doped with at least one selected dopant substance.

5. The system of claim 1, wherein said functionalizing substance comprises at least one of carboxylic acid and an organic acid.

6. The system of claim 1, wherein said EPV is chosen to be at least one of electrical current, electrical voltage difference, conductance, resistance, impedance, capacitance and inductance.

7. The system of claim 1, wherein said known gas or vapor comprises at least one of $NH_3$ and $NO_2$.

8. The system of claim 1, wherein said carbon nanostructures are intertwined with the layer of fibers of said substrate by dispersing said nanostructures in a volatile solution, coating said substrate with the volatile solution, and allowing said volatile solution to evaporate from said substrate.

9. The system of claim 8, wherein said volatile solution comprises at least one of dimethylformamide, dodecylbenezenesulfonate, and water.

10. A method for estimating humidity present in a gas or vapor in a specified volume, the method comprising:
    functionalizing a fibrous substrate with at least one selected functionalizing substance, said substrate having a layer of fibers;
    drop casting a plurality of carbon nanostructures with the layer of fibers of the substrate thereby intertwining the plurality of carbon nanostructures with the layer of fibers in the substrate;
    providing electrical parameter value (EPV) measurement mechanism (EPVMM) that is electrically connected to the substrate at two or more spaced apart locations and that provides a measured EPV that characterizes an electrical path between the two or more spaced apart locations;
    exposing the substrate to a known gas or vapor that has an associated relative humidity value (RH) that is not yet known; and
    providing a processor that receives a measured EPV for the known gas or vapor and that provides an estimate of relative humidity value of the known gas or vapor that corresponds to the measured EPV.

11. The method of claim 10, further comprising choosing said nanostructures to comprise single wall nanotubes and multi-wall nanotubes.

12. The method of claim 10, further comprising choosing said fibrous substrate to comprise at least one of cellulose paper, filter paper, porous paper, and biodegradable paper.

13. The method of claim 10, further comprising doping said substrate with at least one selected dopant substance.

14. The method of claim 10, further comprising choosing said functionalizing substance to comprise at least one of carboxylic acid and an organic acid.

15. The method of claim 10, further comprising choosing said EPV to be at least one of electrical current, electrical voltage difference, conductance, resistance, impedance, capacitance and inductance.

16. The method of claim 10, further comprising choosing said known gas or vapor to comprise $NH_3$ and $NO_2$.

17. The method of claim 10, further comprising intertwining said carbon nanostructures with the layer of fibers of said substrate by dispersing said nanostructures in a volatile solution, coating said substrate with the volatile solution, and allowing said volatile solution to evaporate from said substrate.

18. The method of claim 17, further comprising choosing said volatile solution to comprise at least one of dimethylformamide, dodecylbenezenesulfonate, and water.

19. A method for estimating a concentration of $NH_3$ present in a gas or vapor in a specified volume, the method comprising:
    functionalizing a fibrous substrate with at least one selected functionalizing substance, said substrate having a layer of fibers;
    drop casting a plurality of carbon nanostructures with the layer of fibers of the substrate thereby intertwining the plurality of carbon nanostructures with the layer of fibers in the substrate;
    providing an electrical parameter value (EPV) measurement mechanism that is electrically connected to the substrate at two or more spaced apart locations and that provides a measured EPV that characterizes an electrical path between the two or more spaced apart locations;
    exposing the substrate to a known gas or vapor that has an associated $NH_3$ concentration whose $[NH_3]$ concentration value is not yet known; and
    providing a processor that receives a measured EPV for the known gas or vapor and that provides an estimate of the $[NH_3]$ concentration value of the known gas or vapor that corresponds to the measured EPV value.

20. The method of claim 19, further comprising:
determining relative humidity RH of said known gas or vapor; and
increasing or decreasing said measured EPV by a compensation increment that varies approximately linearly with variation of the RH relative to a reference value of RH.

* * * * *